United States Patent
Tashiro (10) Patent No.: US 9,289,189 B2
(45) Date of Patent: Mar. 22, 2016

(54) ULTRASOUND DIAGNOSTIC APPARATUS

(71) Applicant: FUJIFILM Corporation, Tokyo (JP)

(72) Inventor: Rika Tashiro, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/851,874

(22) Filed: Mar. 27, 2013

(65) Prior Publication Data

US 2013/0261449 A1  Oct. 3, 2013

(30) Foreign Application Priority Data

Apr. 2, 2012  (JP) .................................. 2012-083696

(51) Int. Cl.
*A61B 8/08* (2006.01)
*A61B 8/00* (2006.01)

(52) U.S. Cl.
CPC ............... *A61B 8/461* (2013.01); *A61B 8/0891* (2013.01); *A61B 8/0858* (2013.01); *A61B 8/5223* (2013.01)

(58) Field of Classification Search
None
See application file for complete search history.

(56) References Cited

U.S. PATENT DOCUMENTS

| | | | | |
|---|---|---|---|---|
| 5,831,632 A * | 11/1998 | Schuster et al. | ............... | 345/441 |
| 6,063,030 A * | 5/2000 | Vara et al. | ..................... | 600/437 |
| 6,436,040 B1 * | 8/2002 | Collamore et al. | ........... | 600/437 |
| 6,468,212 B1 * | 10/2002 | Scott et al. | ..................... | 600/437 |
| 7,106,479 B2 * | 9/2006 | Roy et al. | ..................... | 358/3.27 |
| 8,046,707 B2 * | 10/2011 | Akaki | ........................... | 715/767 |
| 8,343,053 B2 * | 1/2013 | Feng et al. | .................... | 600/443 |
| 2004/0207661 A1 * | 10/2004 | Akaki | ........................... | 345/764 |
| 2008/0171939 A1 * | 7/2008 | Ishihara | ....................... | 600/449 |
| 2008/0196506 A1 * | 8/2008 | Satoh et al. | .................... | 73/629 |

(Continued)

FOREIGN PATENT DOCUMENTS

| CN | 1548008 A | 11/2004 |
|---|---|---|
| CN | 101802871 A | 8/2010 |

(Continued)

OTHER PUBLICATIONS

Stein, James H., et al. "Use of Carotid Ultrasound to Identify Subclinical Vascular Disease and Evaluate Cardiovascular Disease Risk: A Consensus Statement from the American Society of Echocardiography Carotid Intima-Media Thickness Task Force Endorsed by the Society for Vascular Medicine." Journal of the American Society of Echocardiography 21.2 (.*

(Continued)

*Primary Examiner* — Christopher Cook
*Assistant Examiner* — Carolyn Pehlke
(74) *Attorney, Agent, or Firm* — McGinn IP Law Group, PLLC (57) ABSTRACT

An ultrasound diagnostic apparatus includes a monitor displaying an ultrasound image, an operating unit receiving an operating instruction from an operator and a control unit controlling a diagnostic apparatus body. The control unit causes measurement calipers each having a measurement line extending linearly in a vertical direction and a gate portion including an upper gate line and a lower gate line which are disposed parallel to each other on the measurement line to be displayed in a superimposed manner on the ultrasound image displayed on the monitor based on the operating instruction from the operating unit, and measurement is sequentially performed at more than one measurement site using the gate portion of each of the measurement calipers which is capable of rotation and change of the distance between the upper gate line and the lower gate line.

16 Claims, 10 Drawing Sheets

(56) References Cited

U.S. PATENT DOCUMENTS

| | | | | |
|---|---|---|---|---|
| 2009/0306514 A1* | 12/2009 | Imamura et al. | | 600/458 |
| 2010/0215245 A1* | 8/2010 | Olivan Bescos | | 382/133 |
| 2010/0260383 A1* | 10/2010 | Truyen et al. | | 382/106 |
| 2010/0321324 A1* | 12/2010 | Fukai et al. | | 345/173 |
| 2012/0108971 A1* | 5/2012 | Miyama et al. | | 600/443 |

FOREIGN PATENT DOCUMENTS

| | | | | |
|---|---|---|---|---|
| JP | 06-125893 A | 5/1994 | | |
| JP | 2004-208858 A | 7/2004 | | |
| JP | 2004-305236 A | 11/2004 | | |
| WO | WO 9706512 A2 * | 2/1997 | | G06T 15/00 |

OTHER PUBLICATIONS

Ikeda, Nobutaka, et al. "Carotid artery intima-media thickness and plaque score can predict the SYNTAX score." European heart journal 33.1 (2012): 113-119 (online publish-ahead-of-print datet: Oct. 25, 2011).*

Chinese Office Action dated Dec. 1, 2015 with an English translation.

* cited by examiner

ULTRASOUND DIAGNOSTIC APPARATUS

BACKGROUND OF THE INVENTION

The present invention relates to an ultrasound diagnostic apparatus and a method of producing an ultrasound image. The invention more particularly relates to an ultrasound diagnostic apparatus which produces an ultrasound image based on reception signals obtained by transmission and reception of ultrasonic waves from and in an ultrasound probe and displays the produced ultrasound image on a monitor.

Heretofore, ultrasound diagnostic apparatuses that use ultrasound images have been put to practical use in the medical field. Generally in this type of ultrasound diagnostic apparatuses, a transducer array of an ultrasound probe transmits ultrasonic beams toward the inside of a subject and receives ultrasonic echoes from the subject, and the diagnostic apparatus body electrically processes reception signals to produce an ultrasound image.

An ultrasound diagnostic apparatus has recently been developed which performs various examinations based on ultrasound images and assists in the examinations themselves so that even an operator who lacks experience and knowledge can perform accurate examinations. For example, JP 6-125893 A discloses an ultrasound diagnostic apparatus capable of measuring the length of a measurement site of an ultrasound diagnostic image by setting a starting point caliper marker and a moving caliper marker to both the ends of the measurement site, respectively. JP 2004-305236 A discloses an ultrasound diagnostic apparatus including two linear calipers which are parallel to each other and are capable of rotation and translation with the calipers kept parallel to each other. JP 2004-208858 A discloses an ultrasound diagnostic apparatus including measurement calipers capable of line type change, highlighting and the like.

With such ultrasound diagnostic apparatuses, even an operator who lacks experience and knowledge can perform efficient and accurate examinations without being confused by the operation.

SUMMARY OF THE INVENTION

However, in the case of measuring at more than one point on a produced ultrasound image using a conventional ultrasound diagnostic apparatus, an operator who is unfamiliar with a series of examinations or the operation of the measurement calipers may take extremely much time or provide inaccurate measurement results.

An object of the present invention is to provide an ultrasound diagnostic apparatus capable of accurate and easy measurement at a plurality of points on an ultrasound image.

In order to achieve the above object, the invention provides an ultrasound diagnostic apparatus which transmits ultrasonic waves from an ultrasound probe toward a subject, produces an ultrasound image in a diagnostic apparatus body based on reception data obtained and displays the produced ultrasound image on a monitor, the ultrasound diagnostic apparatus comprising: an operating unit receiving an operating instruction from an operator; and a control unit controlling the diagnostic apparatus body, wherein the control unit receives the operating instruction from the operating unit, and wherein measurement calipers, each having a measurement line and a gate portion capable of rotation and translation along the measurement line, are displayed on the monitor so that measurement lines of the measurement calipers are parallel to and spaced apart from each other at a predetermined distance in order to measure a distance at more than one measurement site on the ultrasound image.

Each of the measurement calipers is capable of translation, so as to change a distance between a caliper and adjacent measurement caliper according to the operating instruction from the operating unit.

Preferably, the control unit causes the monitor to display auxiliary lines according to the operating instruction from the operating unit and, after the auxiliary lines are moved on the ultrasound image by the operator, the control unit causes the monitor to display the measurement calipers so that the measurement calipers coincide with the auxiliary lines.

The control unit may receive from the operating unit a notice of completion of measurement using one of the measurement calipers and cause the monitor to display a measurement caliper to be used next.

The control unit may receive from the operating unit a notice of completion of measurement using one of the measurement calipers and delete a displayed measurement line of the one of the measurement calipers after the completion of the measurement.

The control unit may cause the monitor to display the measurement calipers and to highlight one operable measurement caliper selected from among the measurement calipers.

According to the invention, the control unit causes the monitor to display measurement calipers each having a measurement line and a gate portion capable of translation along the measurement line and rotation so that the measurement lines of the measurement calipers are parallel to and spaced apart from each other at a predetermined distance, and therefore accurate and easy measurement can be performed with high efficiency at more than one point on an ultrasound image.

DETAILED DESCRIPTION OF THE INVENTION

Embodiments of the invention will be described below based on the accompanying drawings.

Embodiment 1

Figure 1:
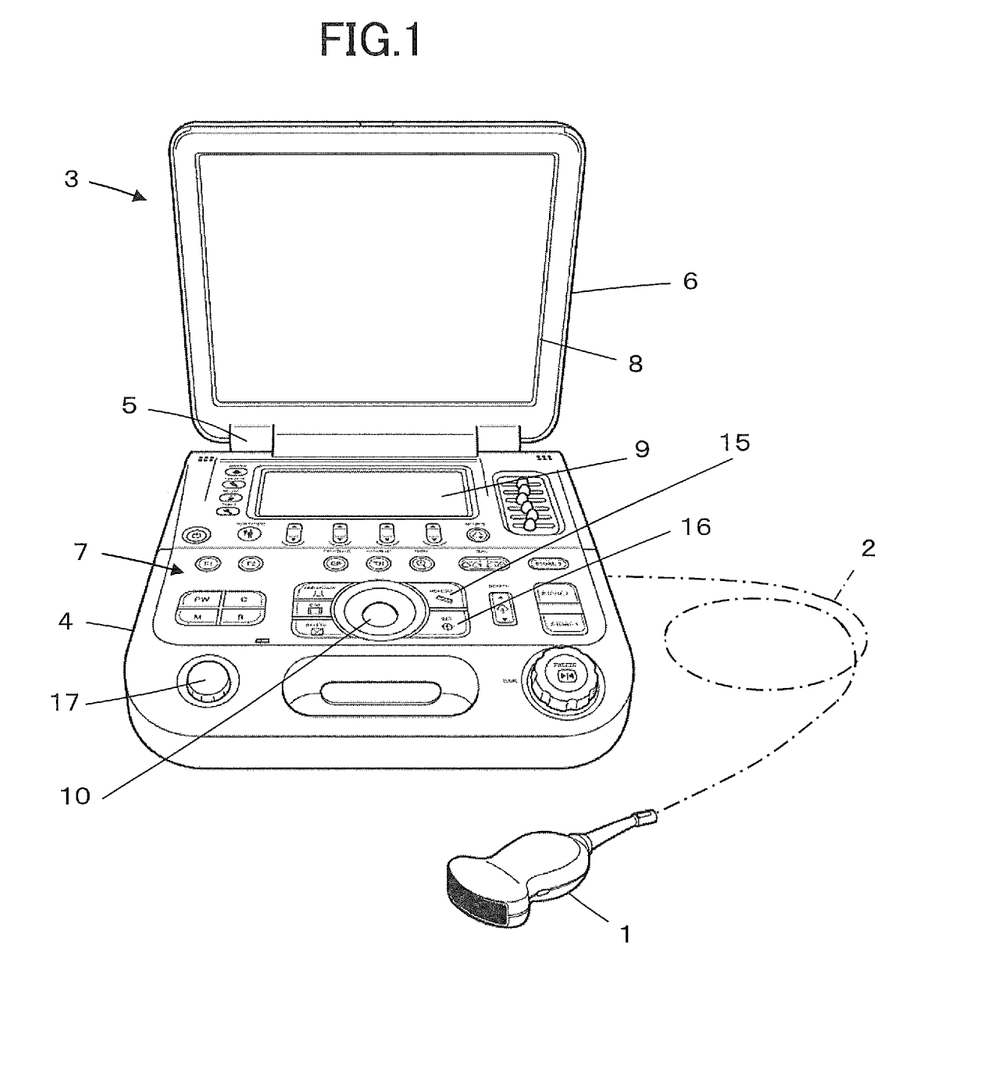
FIG. 1 is a perspective view showing an ultrasound diagnostic apparatus according to Embodiment 1 of the invention.

FIG. 1 shows an ultrasound diagnostic apparatus according to Embodiment 1 of the invention. The ultrasound diagnostic apparatus includes an ultrasound probe 1, and a diagnostic apparatus body 3 which is connected to the ultrasound probe 1 via a communication cable 2.

The diagnostic apparatus body 3 includes a housing 4 and a cover 6 rotatably attached to one end of the housing 4 via hinge portions 5. The housing 4 is substantially in the shape of a flat plate and has an operating unit 7 formed on its surface to enable an operator to perform various operations. A touch panel 9 is provided on the side of the operating unit 7 closer to the hinge portions 5. The cover 6 is also substantially in the shape of a flat plate and has an image monitor 8 formed on the internal surface of the cover 6 which is opposed to the operating unit 7 of the housing 4 by rotating it about the hinge portions 5. The operating unit 7 is provided with a trackball 10, a measurement button 15, a set button 16, a dial 17 and the like.

Figure 2:
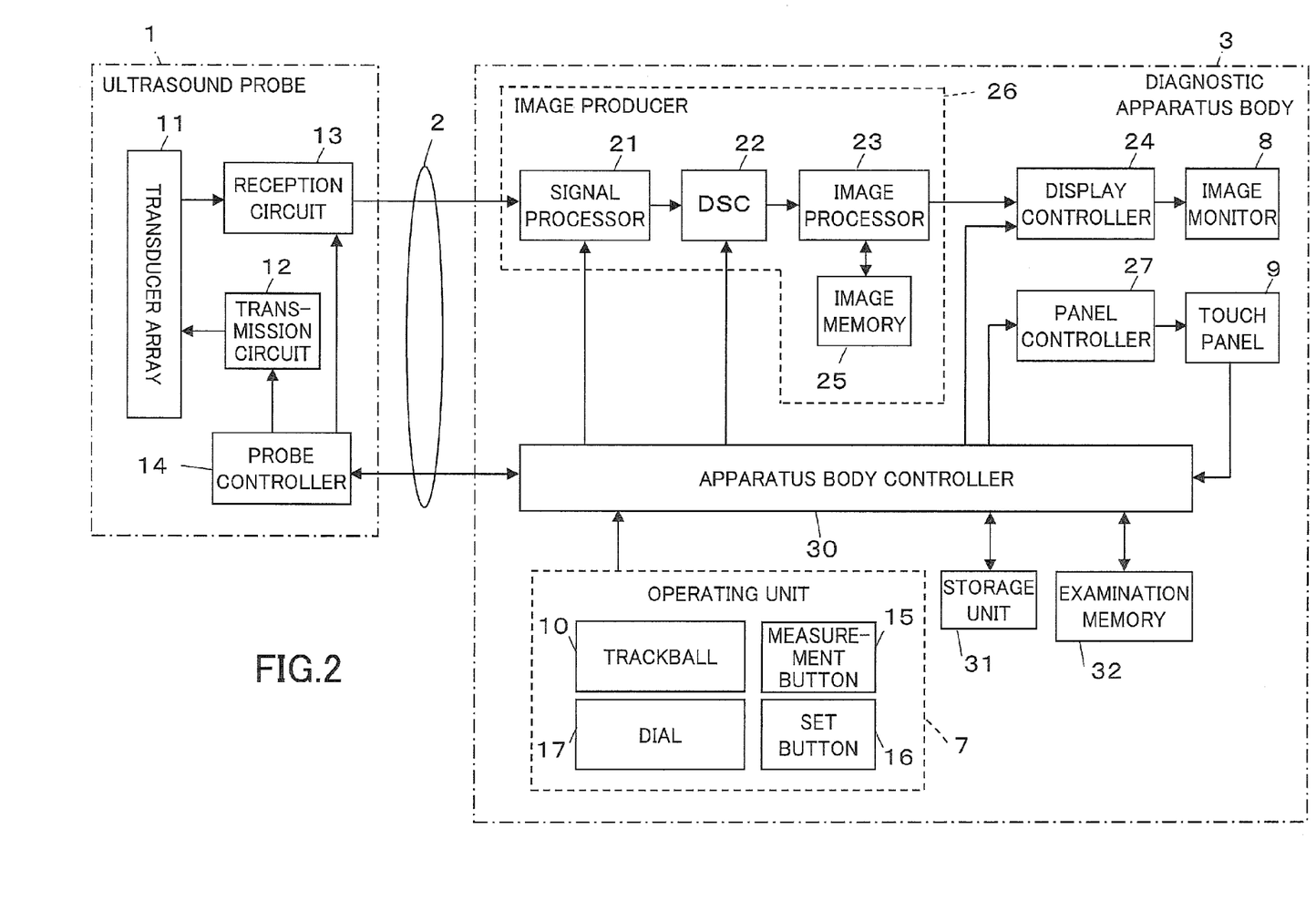
FIG. 2 is a block diagram showing the internal configuration of the ultrasound diagnostic apparatus according to Embodiment 1.

The internal configurations of the ultrasound probe 1 and the diagnostic apparatus body 3 are shown in FIG. 2.

The ultrasound probe 1 has a transducer array 11, which is connected to a transmission circuit 12 and a reception circuit 13, which in turn are connected to a probe controller 14.

The diagnostic apparatus body 3 includes a signal processor 21 connected to the reception circuit 13 of the ultrasound probe 1 via the communication cable 2; the signal processor 21 is connected in sequence to a DSC (Digital Scan Converter) 22, an image processor 23, a display controller 24, and the image monitor 8. The image processor 23 is connected to an image memory 25, and the signal processor 21, the DSC 22, the image processor 23 and the image memory 25 constitute an image producer 26. A panel controller 27 is connected to the touch panel 9.

In addition, the signal processor 21, the DSC 22, the display controller 24 and the panel controller 27 are connected to an apparatus body controller 30, which in turn is connected to the operating unit 7, a storage unit 31, an examination memory 32 and the touch panel 9.

The probe controller 14 of the ultrasound probe 1 and the apparatus body controller 30 of the diagnostic apparatus body 3 are connected to each other via the communication cable 2.

The transducer array 11 of the ultrasound probe 1 includes a one-dimensional or two-dimensional array of ultrasound transducers. These ultrasound transducers each transmit ultrasonic waves to a subject according to drive signals supplied from the transmission circuit 12, receive ultrasonic echoes from the subject and output reception signals. Each of the ultrasound transducers includes a vibrator having a piezoelectric body and electrodes provided on both ends of the piezoelectric body, and the piezoelectric body is made of, for example, a piezoelectric ceramic material typified by PZT (lead zirconate titanate), a piezoelectric polymer typified by PVDF (polyvinylidene fluoride) or a piezoelectric single crystal typified by PMN-PT (lead magnesium niobate-lead titanate solid solution).

When a pulsed voltage or a continuous-wave voltage is applied to the electrodes of such a vibrator, the piezoelectric body expands and contracts to cause the vibrator to generate pulsed or continuous ultrasonic waves and these ultrasonic waves are combined to form an ultrasonic beam. Upon reception of propagating ultrasonic waves, the vibrator expands and contracts to produce electric signals, which are then outputted as signals of the received ultrasonic waves.

The transmission circuit 12 includes, for example, a plurality of pulsers and adjusts the delay amounts of drive signals based on a transmission delay pattern selected according to a control signal from the probe controller 14 so that the ultrasonic waves transmitted from the ultrasound transducers of the transducer array 11 form an ultrasonic beam, and supplies the ultrasound transducers with adjusted drive signals.

The reception circuit 13 subjects the reception signals transmitted from the ultrasound transducers of the transducer array 11 to amplification and A/D conversion, and then performs reception focusing processing by providing the reception signals with respective delays according to the sonic speed or sonic speed distribution that is set based on a reception delay pattern selected according to the control signal from the probe controller 14 and adding them up. This reception focusing processing yields reception data (sound ray signals) where the ultrasonic echoes are well focused.

The probe controller 14 controls the respective components of the ultrasound probe 1 based on various control signals transmitted from the apparatus body controller 30 of the diagnostic apparatus body 3.

The signal processor 21 of the diagnostic apparatus body 3 corrects the attenuation in the reception data produced by the reception circuit 13 of the ultrasound probe 1 according to the distance, i.e., the depth at which the ultrasonic waves are reflected, and then performs envelope detection processing to produce a B mode image signal, which is tomographic image information on a tissue inside the subject's body.

The DSC 22 converts the B mode image signal produced in the signal processor 21 into an image signal compatible with an ordinary television signal scanning mode (raster conversion).

The image processor 23 performs various necessary processing including gradation processing on the B mode image signal entered from the DSC 22 before outputting the B mode image signal to the display controller 24 or storing the B mode image signal in the image memory 25.

The display controller 24 causes the image monitor 8 to display an ultrasound diagnostic image based on the B mode image signal having undergone image processing in the image processor 23.

The image monitor 8 includes a display device such as an LCD, for example, and displays an ultrasound diagnostic image under the control of the display controller 24. At the time of examination, examination tools such as measurement calipers and auxiliary lines to be described later are displayed as required in a superimposed manner on an ultrasound diagnostic image.

The operating unit 7 is disposed on the surface of the housing 4 and has various operating buttons with which an operator performs input operations. Typical exemplary operating buttons include the trackball 10, the measurement button 15, the set button 16 and the dial 17.

For example, the trackball 10 is used to move a measurement caliper or an auxiliary line to be described later, the measurement button 15 to start the measurement, the set button 16 to establish the measurement content, the dial 17 to rotate the gate portion of a measurement caliper or an auxiliary line to be described later.

The storage unit 31 stores, for example, operation programs and examination programs, and recording media such as a hard disk, a flexible disk, an MO, an MT, a RAM, a CD-ROM, a DVD-ROM, an SD card, a CF card, and a USE memory, or a server may be used.

The examination memory 32 is a memory in which information on the examination results including measured values obtained by the examinations is stored.

The apparatus body controller 30 receives various operating instructions entered by the operator using the operating unit 7 as operation signals and controls the respective components in the diagnostic apparatus body 3 based on the operation signals.

The signal processor 21, the DSC 22, the image processor 23, the display controller 24, and the panel controller 27 are each constituted by a CPU and an operation program for causing the CPU to perform various kinds of processing, but they may be each constituted by a digital circuit.

The panel controller 27 may cause the touch panel 9 to display an operation display image outputted from the apparatus body controller 30.

The touch panel 9 is a device including the display function and the position input function in combination, and a transparent membrane sensor for detecting that an operator touched the display device such as an LCD is attached to the touch panel 9 so that a predetermined operation signal is outputted based on the representation on the display and the position on the membrane sensor at which the operator touched the membrane sensor. Detection systems such as resistive system and capacitive system may be used in the membrane sensor.

The operation entered using the touch panel 9 is outputted to the apparatus body controller 30 as an operation signal to cause the apparatus body controller 30 to perform a specified operation.

The touch panel 9 may be replaced by an operation monitor and an operation selector.

Next, the operation of Embodiment 1 will be described.

Pressing a power switch provided in the operating unit 7 of the housing 4 in the diagnostic apparatus body 3 causes electric power to be supplied to the respective components in the diagnostic apparatus body 3 and the ultrasound probe 1 to start the ultrasound diagnostic apparatus.

The ultrasound transducers of the transducer array 11 sequentially transmit ultrasonic waves according to the drive signals from the transmission circuit 12 of the ultrasound probe 1, and the reception signals received by the respective ultrasound transducers are sequentially outputted to the reception circuit 13, where reception data is produced. The image producer 26 of the diagnostic apparatus body 3 produces image signals based on the reception data and the display controller 24 causes the image monitor 8 to display an ultrasound image based on the image signals.

Next, a desired examination is performed based on the ultrasound image produced and displayed on the image monitor 8.

For example, a series of examination items for performing a series of examinations are displayed in blocks on the touch panel 9 of the housing 4. The series of examination items are preset in a plurality of examination programs stored in the storage unit 31 and one examination program can also be displayed by being invoked from the storage unit 31 through the operating unit 7 and the apparatus body controller 30. Alternatively, the operating unit 7 or the touch panel 9 may be operated to prepare a new series of examination items.

When the measurement button 15 is operated to start an examination, a measurement caliper is displayed in a superimposed manner on an ultrasound image on the image monitor 8 through the apparatus body controller 30.

Figure 3:
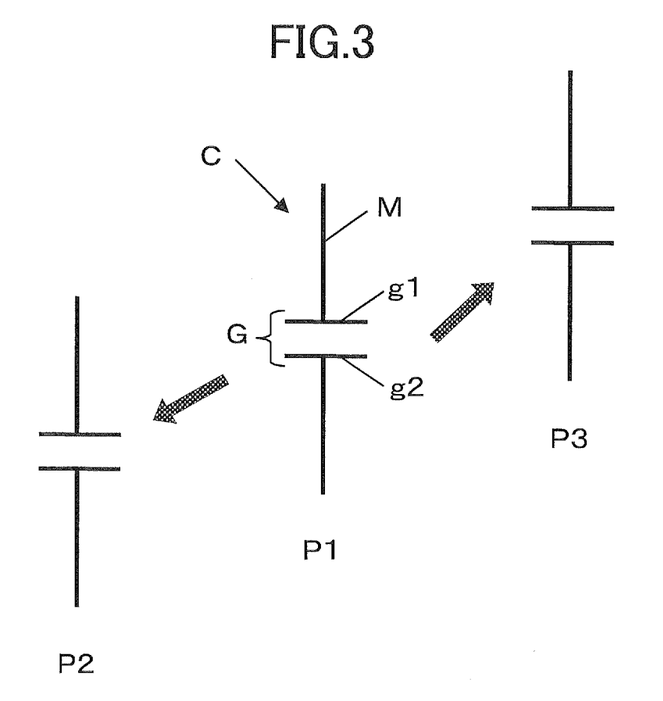
FIG. 3 is a diagram showing how a measurement caliper used in Embodiment 1 is translated up and down or from side to side.

As shown in FIG. 3, a measurement caliper C includes a measurement line M extending linearly in a vertical direction and a gate portion G disposed on the measurement line M. The gate portion G includes an upper gate line g1 and a lower gate line g2 which are parallel to each other. The measurement line M inside the gate portion G is not shown.

The measurement caliper C can be translated up or down or from side to side in response to the operation of the trackball 10 and be moved, for example, from Position P1 to Position P2 or Position P3.

Figure 4:
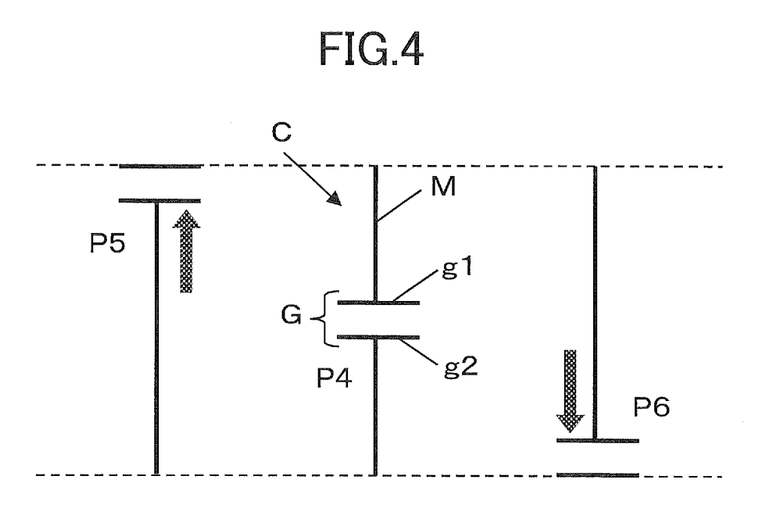
FIG. 4 is a diagram showing how the gate portion of the measurement caliper used in Embodiment 1 is moved up and down along a measurement line.

As shown in FIG. 4, it is also possible to move up or down the gate portion G of the measurement caliper C on the measurement line M by operating the dial 17 after pressing the set button 16. For example, the gate portion G can be moved from Position P4 to Position P5 or Position P6 with the distance between the gates maintained.

Figure 5A:
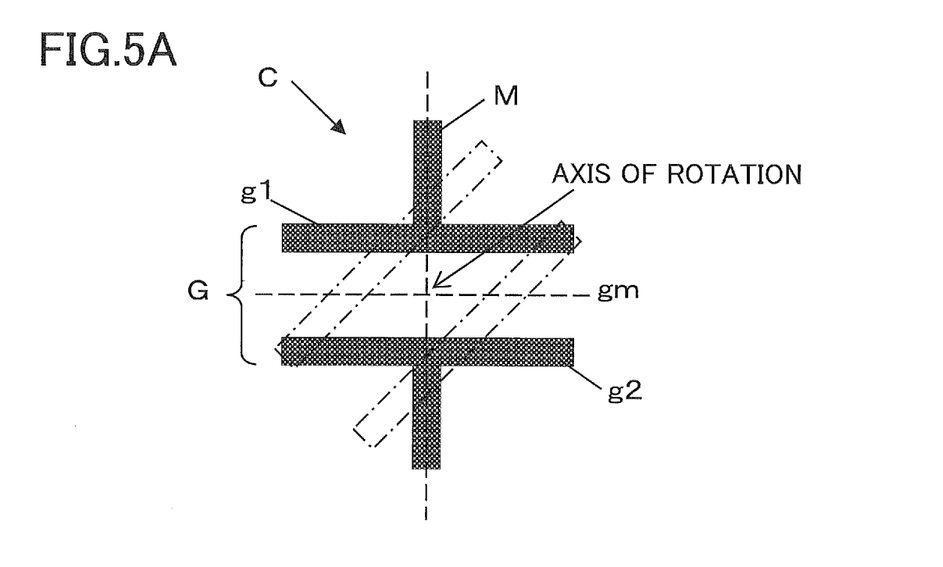
FIG. 5A is a diagram showing that the gate portion of the measurement caliper used in Embodiment 1 is rotatable.
Figure 5B:
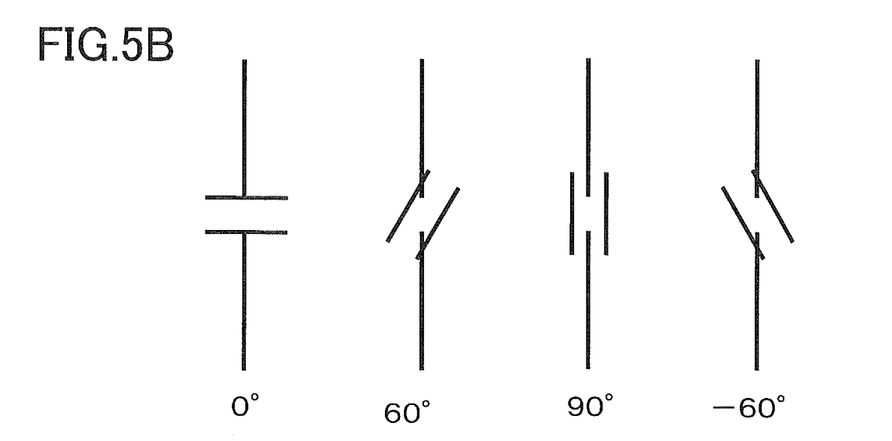
FIG. 5B is a diagram showing the state of the gate portion rotated to various angles.

As shown in FIG. 5A, it is also possible to set as the axis of rotation a point of intersection between the measurement line M and a center line gm which is parallel to the upper gate line g1 and the lower gate line g2 and is drawn in the middle of these gate lines and to rotate the gate portion G of the measurement caliper C about the point of intersection in response to the operation of the dial 17. For example, as shown in FIG. 5B, the gate portion G can be rotated as desired from 0° to 60°, 90° or −60° with the distance between the gates maintained.

Figure 6A:
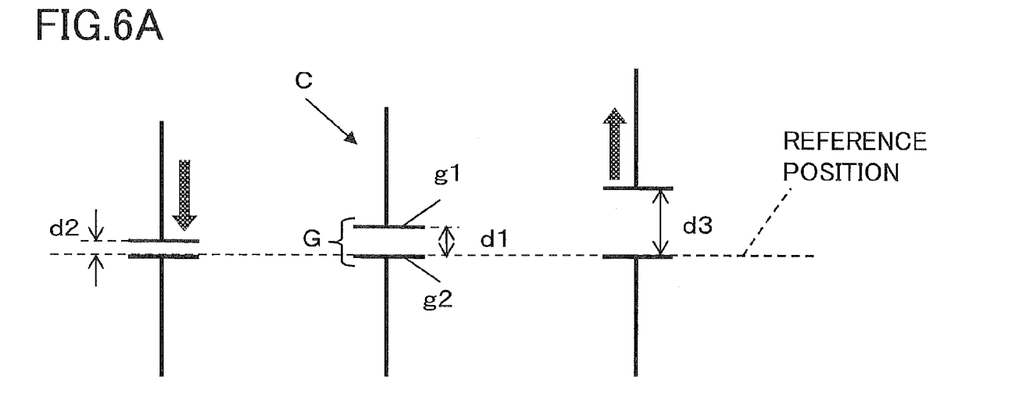
FIG. 6A is a diagram showing the operation before the rotation of the gate portion in changing the distance between the gates in the measurement caliper used in Embodiment 1.

As shown in FIG. 6A, it is also possible to establish the angle of the upper gate line g1 and the lower gate line g2 and the position of the lower gate line g2 in the gate portion G of the measurement caliper C by pressing the set button 16 and to change the distance between the gates, that is, the distance between the mutually parallel upper gate line g1 and lower gate line g2 by operating the trackball 10. Therefore, the distance to the upper gate line g1 from the position of the lower gate line g2 which serves as the reference position can be, for example, decreased from d1 to d2 or increased from d1 to d3.

Figure 6B:
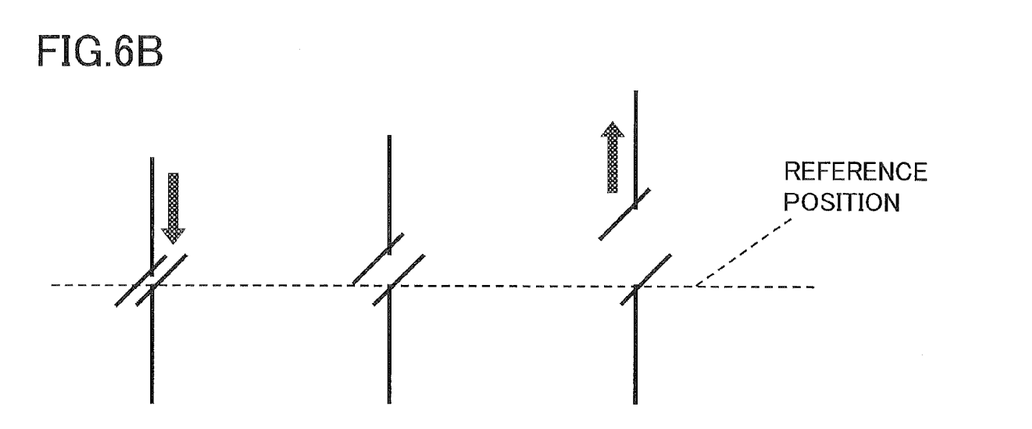
FIG. 6B is a diagram showing the operation after the rotation of the gate portion.

As shown in FIG. 6B, the distance between the gates can also be changed in the same manner in the rotated gate portion G.

Even an operator who is unfamiliar with the operation of the measurement caliper can easily perform accurate measurement by enabling not only the upward, downward, rightward and leftward translational movements of the measurement caliper C but also the movement of the gate portion G on the measurement line M, the rotation of the gate portion G and the change of the distance between the gates.

Next, the operation of the ultrasound diagnostic apparatus according to Embodiment 1 of the invention will be described based on an example of the measurement of IMT (intima-media thickness).

Figure 7:
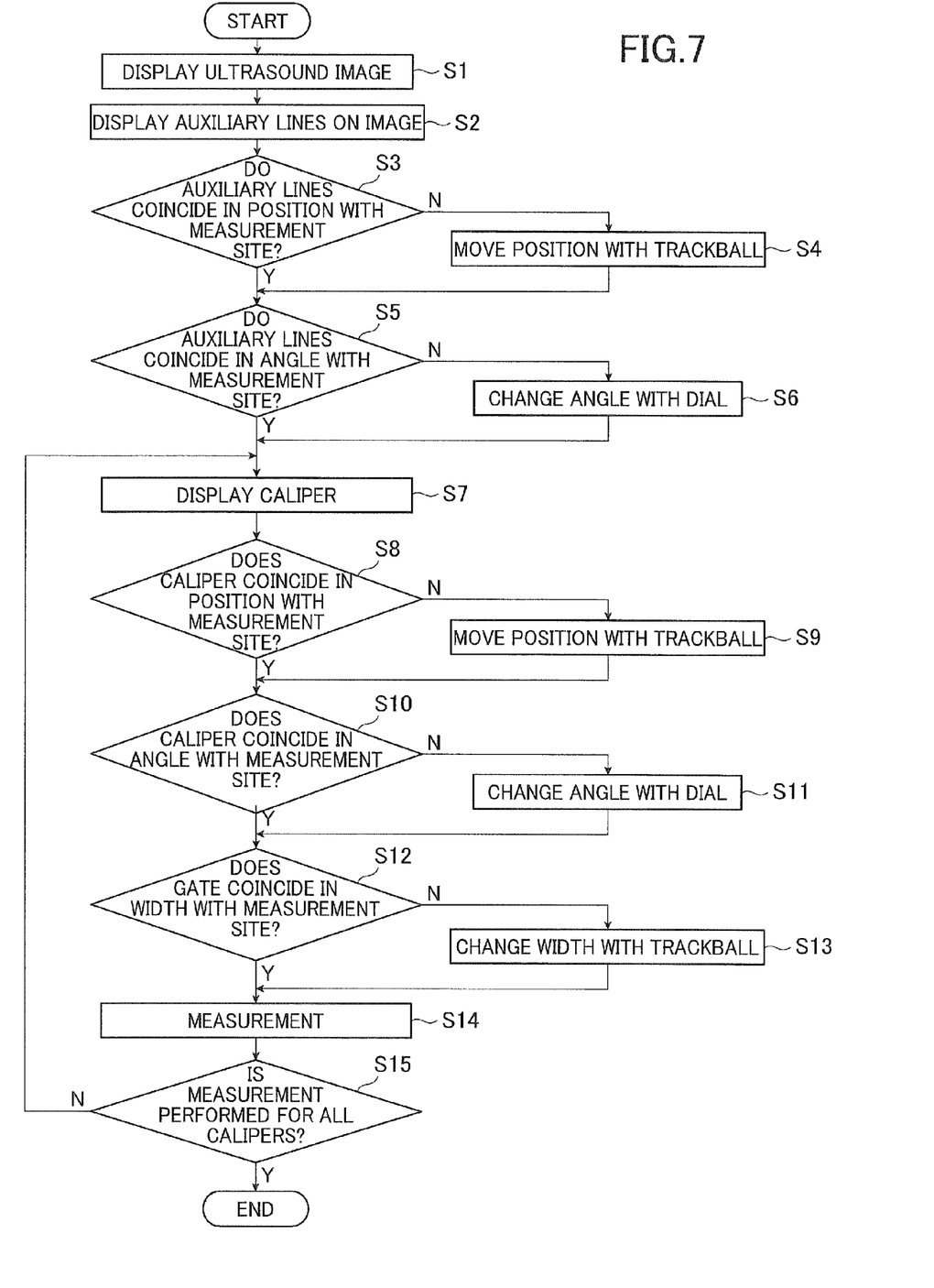
FIG. 7 is a flow chart illustrating the operation in the case where measurement is performed at more than one point on an ultrasound image in Embodiment 1.

FIG. 7 is an exemplary flow chart illustrating the operation in the case where a plurality of measurement calipers are used to perform measurement at more than one point on an ultrasound image; and FIGS. 8A to 8H are diagrams showing step by step the operation of the measurement calipers in the IMT measurement on the proximal wall. The operation of the ultrasound diagnostic apparatus in the IMT measurement will be described below with reference to FIG. 7 and FIGS. 8A to 8H.

First of all, as Step S1, an operator operates the operating unit 7 of the diagnostic apparatus body 3 to display on the image monitor 8 an ultrasound image of a blood vessel for use in the IMT measurement which is stored in the image memory 25.

Figure 8A:
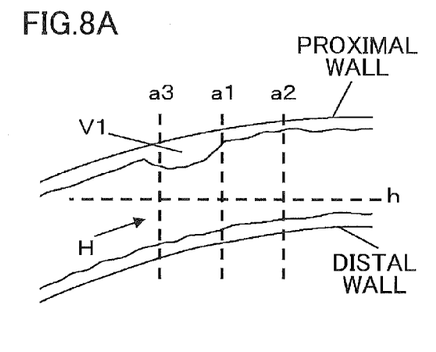
FIGS. 8A to 8H are diagrams showing step by step a method of IMT measurement using the measurement calipers according to Embodiment 1.

The operator confirms that the ultrasound image of the blood vessel is displayed on the image monitor 8 and presses the measurement button 15 of the operating unit 7 to start the IMT measurement as Step S2. In response to the start of the IMT measurement, the apparatus body controller 30 causes, through the display controller 24, the image monitor 8 to display auxiliary lines H in a superimposed manner as shown in FIG. 8A. The auxiliary lines H displayed in the superimposed manner on the ultrasound image are ready for operation using the trackball 10 or the dial 17.

The auxiliary lines H include auxiliary lines a1, a2 and a3 disposed parallel to and spaced apart from each other at a distance of 1.0 cm and an auxiliary line h disposed so as to be perpendicular to the auxiliary lines a1, a2 and a3, and the auxiliary lines are moved or rotated while maintaining the mutual relative positional relationship between the four auxiliary lines a1, a2, a3 and h. The measurement calipers whose number corresponds to the number of auxiliary lines a1 to a3 are prepared.

The above-described auxiliary lines H are not the sole auxiliary lines and the number of auxiliary lines to be displayed, the distance between the displayed auxiliary lines, the relative positional relationship and the like can be preset. Even in the course of an examination, the distance between auxiliary lines displayed on the screen and their relative positional relationship may be adjusted as required.

Next, as Step S3, the operator checks whether the point of intersection between the auxiliary line a1 and the auxiliary line h coincides with a portion V1 having the largest IMT on the proximal wall side of the blood vessel. If the point of intersection does not coincide with the portion V1, the trackball 10 is operated to move the auxiliary lines H in Step S4 so that the point of intersection between the auxiliary line a1 and the auxiliary line h coincides with the portion V1.

Next, as Step S5, the operator checks whether the auxiliary line h extends along the proximal wall of the portion V1 and if it does not, operates the dial 17 to adjust the angle of the auxiliary lines H in Step S6 until the auxiliary line h extends along the proximal wall of the portion V1.

Figure 8B:
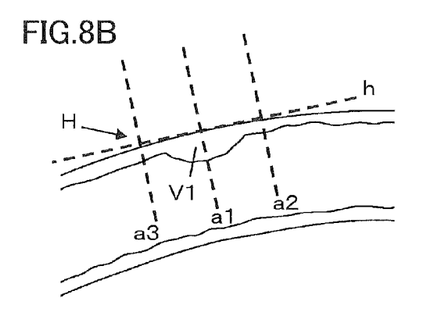

As described above, Steps S3 to S6 permit the auxiliary lines H to be located at positions suitable to the IMT measurement on the proximal wall, as shown in FIG. 8B.

Figure 8C:
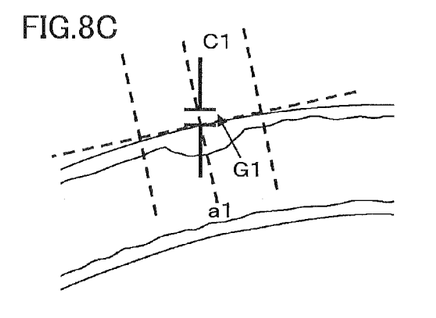

Next, as Step S7, the operator presses the set button 16 to display a first measurement caliper C1 on the point of intersection between the auxiliary line a1 and the auxiliary line h as shown in FIG. 8C. Pressing the set button 16 establishes the positions of the auxiliary lines H, whereupon the newly displayed first measurement caliper C1 is made ready for operation.

As Step S8, the operator checks whether the first measurement caliper C1 is located on the external side of the measurement portion V1 and if it is not, operates the trackball 10 to move the position of the first measurement caliper C1 as Step S9.

Next, as Step S10, the operator checks whether the upper gate line g11 and the lower gate line g12 of the gate portion G1 of the first measurement caliper C1 extend along the measurement portion V1 and if they do not, operates the dial 17 to adjust the angle of the upper gate line g11 and the lower gate line g12 of the gate portion G1 as Step S11. The upper gate line g11 and the lower gate line g12 are always displayed parallel to each other irrespective of the angle of rotation and their angle is changed quite in the same manner by the operation of the dial 17.

Once the angle of the upper gate line g11 and the lower gate line g12 of the gate portion G1 is determined, the operator presses the set button 16. This operation establishes the angle of the upper gate line g11 and the lower gate line g12 and the position of the lower gate line g12 to make the upper gate line g11 ready for movement.

Next, as Step S12, the operator checks whether the width of the gate portion G1, that is, the distance between the upper gate line g11 and the lower gate line g12 coincides with that of the measurement portion V1 and if it does not, operates the trackball 10 to move the upper gate line g11 and change the distance between the upper gate line g11 and the lower gate line g12 as Step S13. The upper gate line g11 can be moved up and down in directions of the measurement line.

Figure 8D:
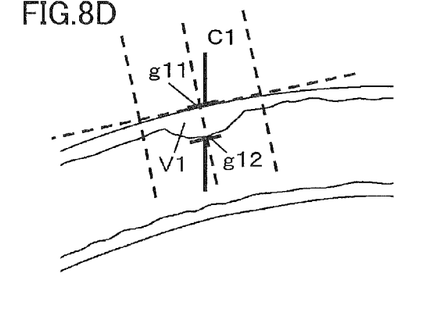

Once the gate portion G1 coincides in width with the measurement portion V1 as shown in FIG. 8D, the operator presses the set button 16 to establish the position of the upper gate line g11 to thereby perform the IMT measurement of the measurement portion V1 as Step S14.

In Step S15, it is checked whether or not the IMT measurement was performed for all the measurement calipers and if there exists a measurement caliper for which the IMT measurement is not performed yet, the process returns to Step S7 to display the next measurement caliper.

Figure 8E:
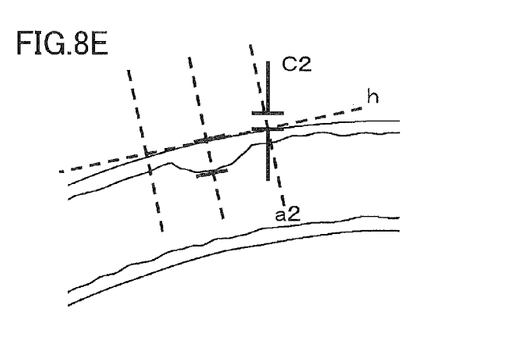
Figure 8F:
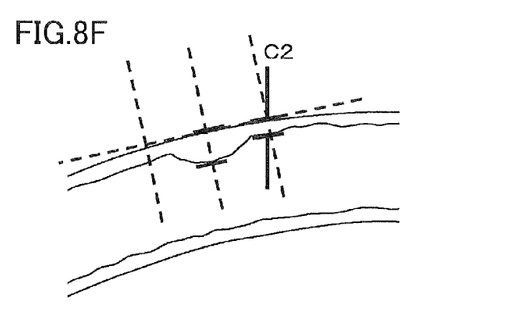

More specifically, upon completion of the IMT measurement using the first measurement caliper C1, a second measurement caliper C2 is displayed in an operable state on the point of intersection between the auxiliary line a2 and the auxiliary line h as shown in FIG. 8E, and the IMT measurement is performed in Steps S7 to S14 as shown in FIG. 8F in the same manner as the first measurement caliper C1. The IMT measurement using the second measurement caliper C2 is performed in the vicinity of the auxiliary line a2 at a distance of 1.0 cm from the first measurement portion V1.

The measurement line M of the measurement caliper C1 with which the measurement has already been completed is deleted as shown in FIGS. 8E and 8F. This enables the clear confirmation of the position measured with the first measurement caliper C1 and the next measurement can be easily performed.

Figure 8G:
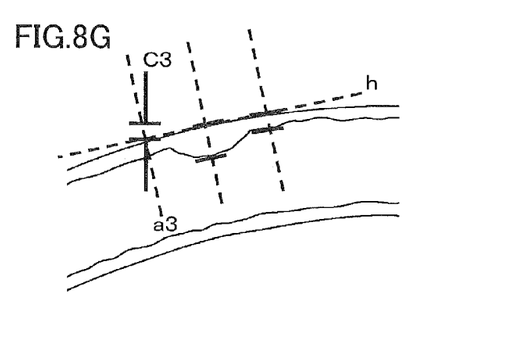

Upon completion of the IMT measurement using the second measurement caliper C2, a third measurement caliper C3 is displayed in an operable state on the point of intersection between the auxiliary line a3 and the auxiliary line h as shown in FIG. 8G, and the IMT measurement is performed in Steps S7 to S14 in the same manner as above. As in the IMT measurement using the second measurement caliper C2, the IMT measurement using the third measurement caliper C3 is performed in the vicinity of the auxiliary line a3 at a distance of 1.0 cm from the first measurement portion V1.

When it is confirmed in Step S15 that the IMT measurement has been completed for all the measurement calipers, the IMT average is calculated in the apparatus body controller 30 to finish the whole measurement. Data obtained by the IMT measurement is stored in the examination memory 32 via the apparatus body controller 30 and displayed on the image monitor 8.

Figure 8H:
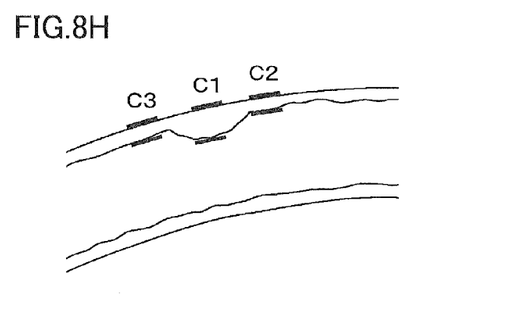

It is of course possible to delete the measurement lines as described above after the end of the whole measurement, and the auxiliary lines H may also be deleted from above the ultrasound image as shown in FIG. 8H. The positions measured with the measurement calipers can be confirmed more clearly.

As described above, even an operator who is unfamiliar with the operation of the measurement calipers and the IMT measurement itself can easily perform accurate measurement by sequentially displaying the measurement calipers on the ultrasound image using the auxiliary lines and sequentially measuring for the operable measurement calipers.

Embodiment 2

Next, the operation of the ultrasound diagnostic apparatus according to Embodiment 2 of the invention will be described based on an example of the plaque score measurement. The configuration of the ultrasound diagnostic apparatus according to Embodiment 2 is the same as that of the apparatus according to Embodiment 1 shown in FIGS. 1 and 2.

The flow of the plaque score measurement according to Embodiment 2 is the same as that in Embodiment 1 shown in FIG. 7.

FIGS. 9A to 9H are diagrams showing step by step the operation of the measurement calipers in the plaque score measurement. The operation of the ultrasound diagnostic apparatus in the plaque score measurement will be described below with reference to FIG. 7 and FIGS. 9A to 9H.

First of all, as Step S1, an operator operates the operating unit 7 of the diagnostic apparatus body 3 to display on the image monitor 8 an ultrasound image of a blood vessel for use in the plaque score measurement which is stored in the image memory 25.

Figure 9A:
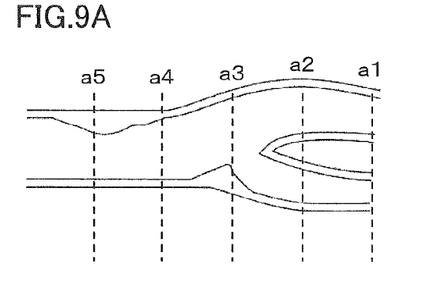
FIGS. 9A to 9H are diagrams showing step by step a method of plaque score measurement using the measurement calipers according to Embodiment 2.

The operator confirms that the ultrasound image of the blood vessel is displayed on the image monitor 8 and presses the measurement button 15 of the operating unit 7 to start the plaque score measurement as Step S2. In response to the start of the plaque score measurement, the apparatus body controller 30 causes, through the display controller 24, the image monitor 8 to display auxiliary lines a1 to a5 as shown in FIG. 9A. The auxiliary lines a1 to a5 are disposed parallel to and spaced apart from each other at a distance of 1.5 cm and are moved or rotated while maintaining the mutual relative positional relationship.

Next, as Step S3, the operator checks whether a branching point of the blood vessel as a reference of the plaque score measurement is located on the auxiliary line a2 or the entire blood vessel is included on the auxiliary lines a1 to a5, and if the branching point of the blood vessel is not located on the auxiliary line a2 or if the entire blood vessel is not included on the auxiliary lines a1 to a5, the operator operates the trackball 10 to move the auxiliary lines a1 to a5 in Step S4. As described above, the auxiliary lines a1 to a5 are moved while maintaining the mutual positional relationship.

Next, as Step S5, the operator checks whether the auxiliary lines a1 to a5 form a substantially right angle with the blood vessel and if it does not, operates the dial 17 to adjust the angle of the auxiliary lines a1 to a5 in Step S6 so that the auxiliary lines a1 to a5 are perpendicular to the blood vessel.

Figure 9B:
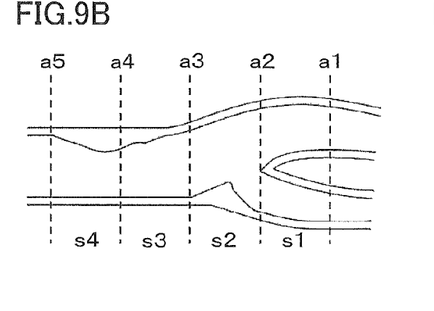

As described above, Steps S3 to S6 permit the auxiliary lines a1 to a5 to be displayed at positions suitable to the plaque score measurement based on the auxiliary line a2, as shown in FIG. 9B, and regions s1 to s4 for measuring the plaque score are determined.

Figure 9C:
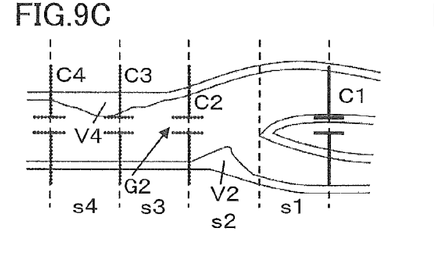

Next, as Step S7, the operator presses the set button 16 to establish the positions of the auxiliary lines a1 to a5. Once the positions of the auxiliary lines a1 to a5 are established, the first measurement caliper C1 to the fourth measurement caliper C4 are displayed in a superimposed manner in the vicinities of the centers of the auxiliary lines a1 and a3 to a5 except the auxiliary line a2 which serves as the reference. Of the first measurement caliper C1 to the fourth measurement caliper C4 displayed in a superimposed manner, at the beginning of the display, the first measurement caliper C1 is selected and highlighted, whereas the other measurement calipers are indicated by dotted lines, as shown in FIG. 9C. The operator operates the trackball 10 to skip the measurement in the region s1 using the first measurement caliper C1, selects the second measurement caliper C2 for measuring the plaque in the measurement portion V2 in the region s2 and presses the set button 16. Once the set button 16 is pressed, the second measurement caliper C2 is highlighted and is made ready for operation. The skipped measurement caliper C1 is not displayed and the other measurement calipers indicated by dotted lines remain displayed at the initial positions.

As Step S8, the operator checks whether the second measurement caliper C2 coincides in position with the measurement portion V2 and if it does not, operates the trackball 10 to move the position of the second measurement caliper C2 as Step S9.

Next, as Step S10, the operator checks whether the upper gate line g21 and the lower gate line g22 of the gate portion G2 of the second measurement caliper C2 extend along the measurement portion V2 and if they do not, operates the dial 17 to adjust the angle of the upper gate line g21 and the lower gate line g22 of the gate portion G2 as Step S11.

Once the angle of the upper gate line g21 and the lower gate line g22 of the gate portion G2 is determined, the operator presses the set button 16. This operation establishes the angle of the upper gate line g21 and the lower gate line g22 and the position of the lower gate line g22 to make the upper gate line g21 ready for movement.

Next, as Step S12, the operator checks whether the gate portion G2 coincides in width with the measurement portion V2 and if it does not, operates the trackball 10 to move the upper gate line g21 and change the distance between the upper gate line g21 and the lower gate line g22 as Step S13. The upper gate line g21 can be moved up and down in directions of the measurement line.

Figure 9D:
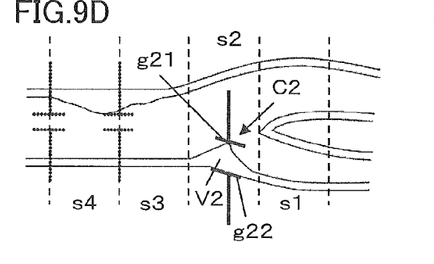

Once the gate portion G2 coincides in width with the measurement portion V2 as shown in FIG. 9D, the operator presses the set button 16 to establish the position of the upper gate line g21 to thereby measure the size of the plaque in the measurement portion V2, that is, the distance between the upper gate line g21 and the lower gate line g22 as Step S14.

Figure 9E:
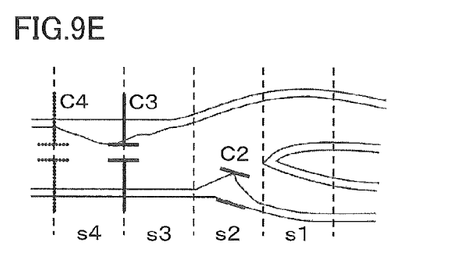

Upon completion of the plaque measurement in the measurement portion V2 using the second measurement caliper C2, the measurement line of the measurement caliper C2 is not displayed as shown in FIG. 9E.

Next, as Step S15, it is checked whether or not the plaque size was measured for all the measurement calipers and if there exists a measurement caliper for which the measurement is not performed yet, the process returns to Step S7.

Figure 9F:
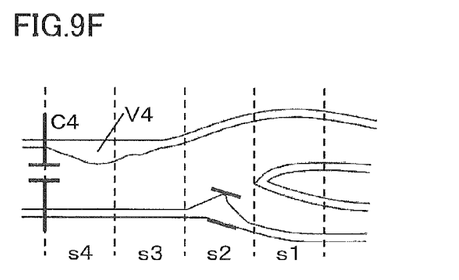

In order to measure the plaque at the measurement portion V4 in the region s4 from the state shown in FIG. 9E, the operator operates the trackball 10 to skip the measurement in the region s3 using the third measurement caliper C3, selects the fourth measurement caliper C4 and presses the set button 16. Once the set button 16 is pressed, the skipped measurement caliper C3 is not displayed and the selected fourth measurement caliper C4 is highlighted as shown in FIG. 9F in the same manner as the above-described second measurement caliper C2 and is made ready for operation.

Figure 9G:
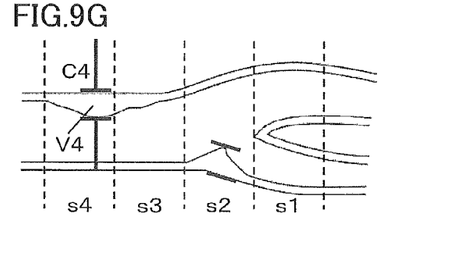

As in the case of the second measurement caliper C2, the size of the plaque at the measurement portion V4 in the region s4 is measured in Steps S7 to S14 using the fourth measurement caliper C4, as shown in FIG. 9G.

Figure 9H:
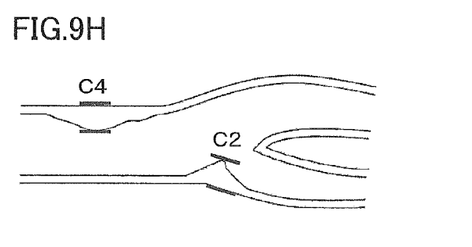

Upon completion of the plaque measurement at the measurement portion V4 using the fourth measurement caliper C4, the measurement line of the fourth measurement caliper C4 is not displayed as shown in FIG. 9H and the plaque score is calculated. The plaque score is a numeric value obtained by summing up the size of the plaques at the portions V2 and V4.

When it is confirmed in step S15 that the plaque measurement has been completed for all the measurement calipers, the whole measurement is finished.

Data obtained by the plaque score measurement is stored in the examination memory 32 via the apparatus body controller 30 and displayed on the image monitor 8.

As shown in FIG. 9H, it is of course possible to delete the measurement lines as described above and also to delete the auxiliary lines from above the ultrasound image after the end of the whole measurement. The positions measured with the measurement calipers can be confirmed more clearly.

It is not necessary to perform the plaque measurement using all the measurement calipers as described above, and the number of measurement calipers for use in the measurement is equal to the number of plaques on the blood vessel ultrasound image.

Therefore, of the measurement calipers C1 to C4 prepared as described above, C2 and C4 corresponding to the portions V2 and V4 are actually used and the measurement is finished without using the other measurement calipers C1 and C3.

Even an operator who is unfamiliar with the operation of the measurement calipers and the plaque score measurement itself can perform accurate measurement in a short period of time with high efficiency by displaying all the measurement calipers on the ultrasound image using auxiliary lines and appropriately skipping unnecessary measurement according to the operator's judgment.

Embodiment 3

Figure 10A:
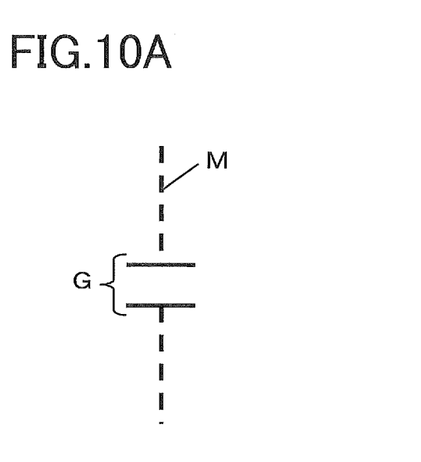
FIGS. 10A and 10B are diagrams each showing a measurement caliper used in Embodiment 3.
Figure 10B:
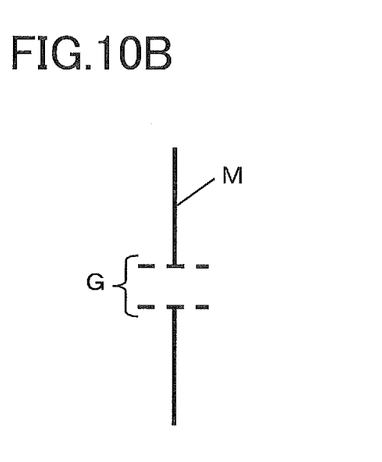

In the ultrasound diagnostic apparatuses in Embodiments 1 and 2, the measurement calipers were indicated by solid lines or dotted lines. However, the measurement line M may be indicated by dotted lines and the gate portion G by solid lines, as shown in FIG. 10A. Alternatively, the measurement line M may be indicated by solid lines and the gate portion G by dotted lines, as shown in FIG. 10B.

Figure 11:
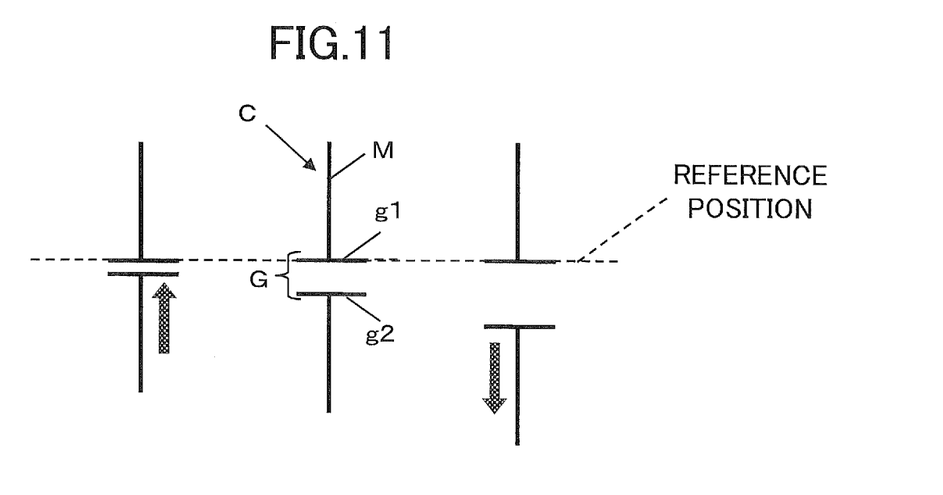
FIG. 11 is a diagram showing how the distance between the gates in the measurement caliper used in a modification of Embodiment 3 is changed.

In the ultrasound diagnostic apparatuses in Embodiments 1 and 2, the gate distance between the upper gate line g1 and the lower gate line g2 was changed by moving the upper gate line g1 in the directions of the measurement line M with the lower gate line g2 fixed. However, the lower gate line g2 may be moved in the directions of the measurement line M with the upper gate line g1 fixed to the contrary, as shown in FIG. 11.

Figure 12A:
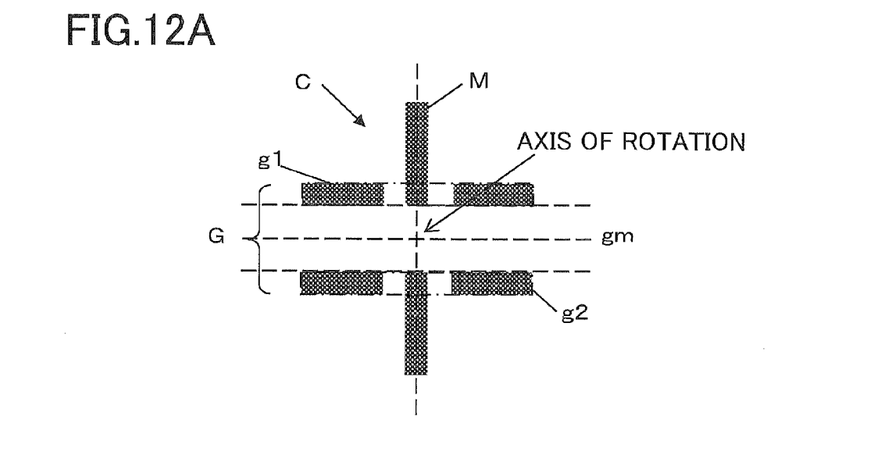
FIG. 12A is a diagram showing the state of the gate portion before its rotation in the measurement caliper used in another modification of Embodiment 3.

In each of the ultrasound diagnostic apparatuses in Embodiments 1 and 2, the intersection between the upper and lower gate lines g1 and g2 and the measurement line M in the gate portion G was displayed but the intersection therebetween may not be displayed over a predetermined distance as shown in FIG. 12A.

Figure 12B:
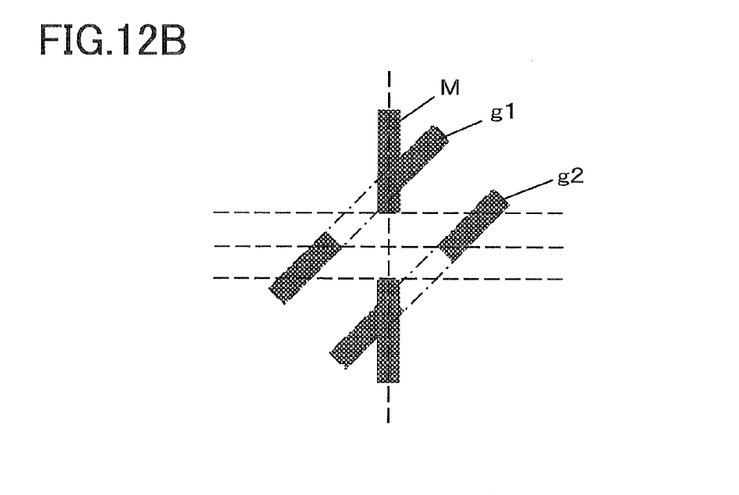
FIG. 12B is a diagram showing the state of the gate portion after its rotation.

The undisplayed state of the intersection between the upper and lower gate lines g1 and g2 and the measurement line M over a predetermined distance particularly enables a part of the ultrasound image hidden by the upper and lower gate lines g1 and g2 to be reduced not only before the rotation of the gate portion G as shown in FIG. 12A but also after the rotation of the gate portion G as shown in FIG. 12B, thereby improving the visibility of the ultrasound image during the operation of the measurement caliper C.

Figure 13:
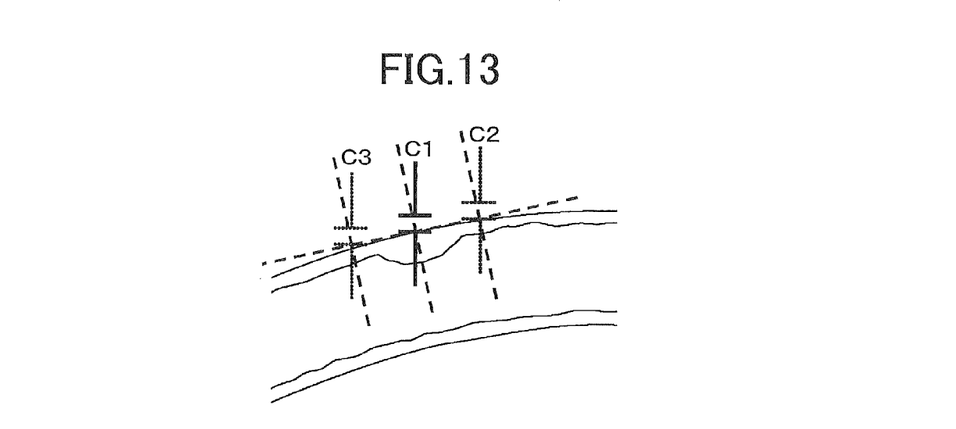
FIG. 13 is a diagram showing a plurality of measurement calipers displayed in a modification of Embodiment 1.

In the above-described Embodiment 1, the operable measurement calipers were sequentially displayed one by one for each measurement. However, the method shown in FIG. 13 may be applied which includes displaying all the measurement calipers, selecting a measurement caliper to be operated from among them and highlighting the selected measurement caliper as in the above-described Embodiment 2.

All the measurement calipers were displayed at a time in the above-described Embodiment 2 but on the contrary the operable measurement calipers may be sequentially displayed one by one for each measurement as in the above-described ultrasound diagnostic apparatus in Embodiment 1.

While the ultrasound diagnostic apparatus of the invention has been described above in detail, the invention is by no means limited to the above embodiments, and various improvements and modifications may be made without departing from the scope and spirit of the invention.

What is claimed is:

1. An ultrasound diagnostic apparatus, comprising:
an ultrasound probe which transmits ultrasonic waves toward a subject and produces reception data; and
a diagnostic apparatus body, comprising:
an image producing circuit which produces an ultrasound image based on the reception data;
a monitor which displays the produced ultrasound image;
an operating console which receives an operating instruction from an operator; and
a control circuit which receives the operating instruction from the operating console and causes the monitor to display:
auxiliary lines superimposed over the ultrasound image and spaced apart from each other at a predetermined distance according to the operating instruction from the operating console, the auxiliary lines being moveable and rotatable while maintaining a mutual relative positional relationship; and
a plurality of measurement calipers superimposed over the ultrasound image and coinciding with the auxiliary lines, the plurality of measurement calipers including:
a plurality of measurement lines which are parallel to and spaced apart from each other at a predetermined distance in order to measure a distance at a plurality of measurement sites on the ultrasound image; and
a plurality of gate portions which are rotatable and translatable along the plurality of measurement lines, respectively,
wherein the auxiliary lines comprise three or more first lines disposed parallel to and spaced apart from each other at the predetermined distance, and a second line disposed so as to be perpendicular to the first lines,
an angle of the auxiliary lines is changed so as to extend the second line along a blood vessel wall of one of the plurality of measurement sites,
a measurement caliper of the plurality of measurement calipers is disposed so as to coincide with a point of intersection between the first lines and the second line changed at the angle, respectively, and
a position of each of the plurality of measurement calipers is changed so as to dispose one of the gate portions of the plurality of measurement calipers on the blood vessel wall of the plurality of measurement sites and on the first lines, respectively.

2. The ultrasound diagnostic apparatus according to claim 1, wherein each of said measurement calipers is capable of translation, so as to change the predetermined distance between said caliper and an adjacent measurement caliper according to said operating instruction from said operating console.

3. The ultrasound diagnostic apparatus according to claim 1, wherein, after said auxiliary lines are moved on said ultrasound image according to said operating instruction from said operating console, said control circuit causes said monitor to display said measurement calipers so that the measurement calipers coincide with said auxiliary lines.

4. The ultrasound diagnostic apparatus according to claim 1, wherein said control circuit receives from said operating console a notice of completion of measurement using one of said measurement calipers and causes said monitor to display a measurement caliper to be used next.

5. The ultrasound diagnostic apparatus according to claim 1, wherein said control circuit receives from said operating console a notice of completion of measurement using one of said measurement calipers and deletes a displayed measurement line of said one of the measurement calipers after the completion of the measurement.

6. The ultrasound diagnostic apparatus according to claim 1, wherein said control circuit causes said monitor to display said measurement calipers at a time, to select one measurement caliper to be operated from among said measurement calipers and to highlight said one operable measurement caliper selected.

7. The ultrasound diagnostic apparatus according to claim 1, wherein the auxiliary lines and the measurement calipers are displayed in a superimposed manner over the ultrasound image.

8. The ultrasound diagnostic apparatus according to claim 1, wherein a number of the measurement calipers is the same as a number of the auxiliary lines.

9. The ultrasound diagnostic apparatus according to claim 1, wherein the gate portion includes an upper gate line and a lower gate line which is parallel to the upper gate line, and a measurement line inside the gate portion (G) is not displayed.

10. The ultrasound diagnostic apparatus according to claim 1, wherein a distance between the upper and lower gate lines is maintained as the gate portion is moved.

11. The ultrasound diagnostic apparatus according to claim 10, wherein the gate portion is rotatable about an axis of rotation on the measurement line, the axis of rotation being a point of intersection between the measurement line and a center line which is parallel to the upper and lower gate lines and is drawn in the middle of upper and lower gate lines.

12. The ultrasound diagnostic apparatus according to claim 10, wherein the measurement calipers are sequentially displayed on the monitor.

13. The ultrasound diagnostic apparatus according to claim 1, wherein the image producing circuit comprises an image memory.

14. A method of performing a measurement at plural points on an ultrasound image, comprising:
displaying an ultrasound image on a monitor;
displaying auxiliary lines superimposed over the ultrasound image on the monitor, the auxiliary lines being spaced apart from each other at a predetermined distance and being movable and rotatable while maintaining a mutual relative positional relationship according to an operating instruction;
adjusting the auxiliary lines to coincide with a plurality of measurement sites on the ultrasound image;
displaying a plurality of measurement calipers superimposed over the ultrasound image and coinciding with the auxiliary lines, the measurement calipers including:
a plurality of measurement lines which are parallel to and spaced apart from each other at a predetermined distance in order to measure a distance at the plurality of measurement sites; and
a plurality of gate portions which are rotatable and translatable along the plurality of measurement sites on the ultrasound image,
wherein the auxiliary lines comprise three or more first lines disposed parallel to and spaced apart from each other at a predetermined distance, and a second line disposed so as to be perpendicular to the first lines,
an angle of the auxiliary lines is changed so as to extend the second line along a blood vessel wall of one of the plurality of measurement sites,
a measurement caliper of the plurality of measurement calipers is disposed so as to coincide with a point of intersection between the first lines and the second line changed at an angle, respectively, and
a position of each of the plurality of measurement calipers is changed so as to dispose one of the gate portions of the plurality of measurement calipers on the blood vessel wall of the plurality of measurement sites and on the first lines, respectively.

15. The method of claim 14, wherein the adjusting of the auxiliary lines comprises adjusting one of a position and an angle of the auxiliary lines, and
wherein the adjusting of the plurality of measurement calipers comprises adjusting one of a position of a measurement caliper of the plurality of measurement calipers, an angle of a measurement caliper of the plurality of measurement calipers, and a width of a gate portion of the plurality of gate portions.

16. The method of claim 14, wherein the displaying of the plurality of measurement calipers comprises sequentially displaying the plurality of measurement calipers.

* * * * *